(12) United States Patent
Zhang et al.

(10) Patent No.: US 7,960,594 B2
(45) Date of Patent: Jun. 14, 2011

(54) METHOD OF PREPARING ETHYLENE GLYCOL FROM CELLULOSE

(76) Inventors: Tao Zhang, Liaoning (CN); Mingyuan Zheng, Liaoning (CN); Na Ji, Liaoning (CN); Aigin Wang, Liaoning (CN); Yuying Shu, Liaoning (CN); Hui Wang, Liaoning (CN); Xiaodong Wang, Liaoning (CN); Jingguang Chen, Liaoning (CN)

( * ) Notice: Subject to any disclaimer, the term of this patent is extended or adjusted under 35 U.S.C. 154(b) by 0 days.

(21) Appl. No.: 12/734,601

(22) PCT Filed: Oct. 31, 2008

(86) PCT No.: PCT/CN2008/072894
§ 371 (c)(1),
(2), (4) Date: May 10, 2010

(87) PCT Pub. No.: WO2010/045766
PCT Pub. Date: Apr. 29, 2010

(65) Prior Publication Data
US 2010/0256424 A1    Oct. 7, 2010

(30) Foreign Application Priority Data
Oct. 24, 2008  (CN) .......................... 2008 1 0228257

(51) Int. Cl.
*C07C 29/00*    (2006.01)

(52) U.S. Cl. ...................................................... 568/861
(58) Field of Classification Search ............ 568/861
See application file for complete search history.

(56) References Cited

U.S. PATENT DOCUMENTS

| | | | | |
|---|---|---|---|---|
| 2,868,847 A | * | 1/1959 | Gilman | 568/863 |
| 4,476,331 A | * | 10/1984 | Dubeck et al. | 568/861 |
| 5,107,018 A | * | 4/1992 | Schuster | 568/863 |
| 5,210,335 A | * | 5/1993 | Schuster et al. | 568/863 |

* cited by examiner

*Primary Examiner* — Sikarl A Witherspoon
(74) *Attorney, Agent, or Firm* — Raymond Y. Chan; David and Raymond Patent Firm

(57) ABSTRACT

A method for preparing ethylene glycol from cellulose uses the cellulose as the feed for the reaction. The cellulose conversion is performed over catalysts which are composed of the metallic state, carbides, nitrides, or phosiphides of molybdenum or tungsten, and metallic cobalt, nickel, ruthenium, rhodium, palladium, iridium, and platinum of the group 8, 9, or 10 transition metals. The catalytic conversion of cellulose is conducted at 120 to 300° C. and hydrogen pressure 1 to 12 MPa under the hydrothermal conditions to achieve the high efficiency, high selectivity, and high yield of ethylene glycol. Compared to the existing method of preparing ethylene glycol from ethylene, the method, using the renewable raw material for the reaction, is friendly to the environment, and has high atom economy.

8 Claims, No Drawings

US 7,960,594 B2

METHOD OF PREPARING ETHYLENE GLYCOL FROM CELLULOSE

BACKGROUND OF THE PRESENT INVENTION

1. Field of Invention

The present invention relates to a method of preparing ethylene glycol from cellulose, and more particularly to a reaction process of cellulose under hydrothermal condition, wherein the cellulose reaction process of the method comprises catalytic degradation and hydrogenation reactions.

2. Description of Related Arts

The ethylene glycol is one of liquid fuels, and also is an important feed for polyester synthesis. For examples, the ethylene glycol can be used for synthesizing polyethylene terephthalate (PET), and polyethylene naphthalene (PEN); the ethylene glycol can also be used as antifreeze agents, lubricant, plasticizers, or surfactant etc. Thus, the ethylene glycol has variety of applications in the organic chemical material.

At present, the industrial process for producing the ethylene glycol is consuming petroleum resources as the raw material, wherein the ethylene glycol is produced via oxidizing ethylene to form epoxyethane, and then hydrating it to obtain the ethylene glycol. (Literature 1: CUI Xiao-ming, the overview of the production development of ethylene glycol, Chemical Industry, 2007, 25, (4), 15-21. Literature 2: Process for preparing ethanediol by catalyzing epoxyethane hydration, Patent No. CN1463960-A; Patent No. CN1204103-C). The conventional method for ethylene glycol production is based on the nonrenewable petroleum sources, and involving the oxidization or epoxidation process, which comprises complicated reaction steps, so that the procedure of preparing ethylene glycol is low efficient, containing high amount of undesired side products, consuming much energy, and causing serious pollutions.

Therefore, finding renewable materials for producing ethylene glycol is able to reduce the dependence on the petroleum, so as to build an eco friendly manufacturing process. Currently, the researches of converting the biomass into ethylene glycol are mostly focusing on starch, glucose, sucrose, and sugar alcohols, such as hexitols, as the raw materials for the conversion therefrom. (Literature 3: Process for the preparation of lower polyhydric alcohols, U.S. Pat. No. 5,107,018. Literature 4: Preparation of lower polyhydric alcohols, U.S. Pat. No. 5,210,335). However, the above mentioned raw materials for the conversion of ethylene glycol are the currently basic food of human beings, so that using them for ethylene glycol production is facing the dilemma of mankind survival and development. Cellulose is the largest renewable resources having rich sources, such as the remaining straw from the agricultural production or the wastes from the forestry, etc., which are low in cost for using as the raw material for the conversion of biomass. Using cellulose for synthesizing ethylene glycol can not only build up a new synthesis process to achieve low cost, but also obtain the high value product of the ethylene glycol. Furthermore, the cellulose is unable to be digested by human beings, so that using the cellulose as the raw material for the ethylene glycol production will not affect the food security and not reduce the food production for the mankind. In addition, the cellulose is formed by the condensation of glycosidic bond of glucose units containing a large number of hydroxyls. Those hydroxyls are fully reserved during the process of cellulose converting into ethylene glycol, which makes the conversion process has a very high atom economy. Therefore, the process of converting cellulose into ethylene glycol has significant advantages over most of the existing processes of making ethylene glycol.

Though there are numbers of advantages of producing polyols from cellulose, cellulose contains a large amount of intermolecular and intramolecular hydrogen bonds, so that the structure of cellulose is very robust. Therefore, the cellulose is usually first hydrolyzed to reducing sugar by acids, and then the obtained glucose is further converted for other uses. The whole process is not only complicated, but also generates the environmental pollution issues. (Literature 4: Two stage hydrogenolysis of carbohydrate to glycols using sulfide modified ruthenium catalyst in second stage, U.S. Pat. No. 4,476,331). The present invention provides a reaction process, which is using water, the most environmental friendly solvent, as the reaction medium, is no need of adding acid or base, and is able to be completed via one step to accomplish the high yield of ethylene glycol from cellulose.

SUMMARY OF THE PRESENT INVENTION

An object of the present invention is to provide a method of preparing ethylene glycol from cellulose, which comprises one step of catalytic hydrogenation of cellulose to ethylene glycol with high yield and high selectivity thereof.

Accordingly, in order to accomplish the above objective, the present invention provides a method of preparing ethylene glycol from cellulose, wherein cellulose is used as feed. A catalyst is added to cellulose, wherein the catalyst comprises two sorts of active components, ascribed to a first active group and a second active group. A first active component of the first active group is one or more metals selected from the transition metals of group 8, 9, or 10, consisting of iron, cobalt, nickel, ruthenium, rhodium, palladium, iridium, and platinum. A second active component of the second active group is one or more materials selected from the group consisting of metallic molybdenum, metallic tungsten, molybdenum carbides, molybdenum nitrides, molybdenum phosphide, tungsten carbides, tungsten nitrides, and tungsten phosphide. The reaction is conducted in a sealed batch reactor, wherein the reactants are stirred therewith. The hydrogen filled in the reactor at room temperature has an initial pressure of 1 to 12 MPa, the reacting temperature is 120-300° C., and the reacting time is no less than 5 minutes. The weight ratio of the second active component to the first active component is in the range of 0.02 to 1600.

The support of the active components includes one or more compositions selected from the group consisting of active carbon, aluminum oxide, silica, zirconia, zinc oxide, and titanium dioxide. The metal loading of the first active component is about 0.05-50 wt %, and the metal loading of the second active component is about 1-80 wt %. Or, the catalysts are metallic skeletal catalysts without supports, such as Raney nickel, wherein the catalyst framework is made of the active components.

The mass ratio of the cellulose to water is 1:200-1:4. The mass ratio of the cellulose to catalyst is 1:1-30:1.

The reactions of each of the embodiments of the present invention are conducted in the high pressure reactor. The reaction can also be conducted in a reactor with a better optimized design to achieve the better mass transfer among the cellulose, hydrogen, and catalyst to obtain a better reaction result.

The present invention has the following advantages.

1. Use the cellulose as the feed, wherein the cellulose has the largest production among the biomass in the natural resources, so that the cellulose has very wide sources, such as from wood, cotton, remaining straw from the agricultural production, so as to minimize material and manufacturing cost. Currently, the most of the industries use ethylene obtained from petroleum as the raw material for synthesizing ethylene glycol. The method of the present invention consumes no fossil energy resources, but uses cellulose of renewable resources, so as to meet the requirement of sustainable development.

2. Compare to other processes using biomass as the feed materials for synthesizing ethylene glycol, such as using the starch, glucose, and fructose as the feed materials for converting into ethylene glycol, the present invention uses cellulose, which is not the sources of food of human beings, so that the present invention minimize the concern of the impact of food safety to human beings.

3. The method is simple, and no requirement of acid hydrolyzing the cellulose, so that the process is able to be completed via one-step conversion of cellulose to accomplish the high yield of ethylene glycol.

4. After the cellulose is catalyzed for degradation thereof, the hydroxyls are fully reserved during the process of cellulose converted into ethylene glycol, which makes the conversion process have a very high atom economy.

5. The reaction is performed under the hydrothermal condition, wherein the cellulose conversion comprising reactions of catalytic degradation and hydrogenation is environmental friendly. Water is used as the reacting medium, wherein no inorganic acid or base is required to be added in the reaction, so that the method of the present invention overcomes the pollutions from the conventional degradation process of cellulose, so as to minimize the environmental pollutions.

6. The reacting process has high yield and high selectivity of the target product, wherein the ethylene glycol yield is about 70%, so that the method has great potential of applications in the future.

To sum up, the present invention provides a method for producing ethylene glycol from cellulose with high yield and high selectivity. Compared to the existing process using ethylene as the feedstock for synthesizing ethylene glycol, the process of the present invention using renewable resource as feeds is environmental friendly and has high atom economy.

The embodiment of the present invention as shown in the following drawings and described below is exemplary only and not intended to be limiting.

DETAILED DESCRIPTION OF THE PREFERRED EMBODIMENT

Example 1 is the Preparation of Metallic Tungsten Catalyst

An active carbon support was impregnated with ammonium metatungstate solution (0.4 g/ml of mass concentration), and then dried at 120° C. for 12 hours. The dried sample was reduced at 700° C. in hydrogen flow for one hour. A metallic tungsten catalyst was obtained (30 wt % tungsten loading).

Example 2 is the Preparation of Metallic Nickel Tungsten Catalyst

Further soak the above tungsten catalyst with nickel nitrate solution, and then dry it at 120° C. The derived sample was reduced at 400° C. in hydrogen flow for 2 hours to obtain a Ni—W/AC catalyst (15% Ni-25% W).

Example 3 is the Preparation of Metallic Platinum Tungsten Catalyst

A silica support was impregnated with ammonium metatungstate solution (0.2 g/ml of mass concentration), and then dried at 120° C. for 12 hours. The derived sample was reduced at 700° C. for one hour in hydrogen flow. $W/SiO_2$ (15 wt % tungsten loading) was obtained. Further impregnate the $W/SiO_2$ with $H_2PtCl_4$ solution and dry it at 120° C. Then, the derived sample was reduced at 350° C. for 2 hours in hydrogen flow. The obtained catalyst was denoted as Pt—$W/SiO_2$ (0.5% Pt-15% W).

Example 4 is the Preparation of a Tungsten Carbide Catalyst

Active carbon support was impregnated with ammonium metatungstate solution (0.4 g/ml of mass concentration), and then dried at 120° C. for 12 hours. The derived sample was reduced at 800° C. for one hour in hydrogen flow for carbothermal reaction to obtain a tungsten carbide catalyst $W_2C/AC$ (30 wt % tungsten loading).

Example 5 is the Preparation of a Tungsten Nitride Catalyst

Active carbon was impregnated with ammonium metatungstate solution (0.2 g/ml of mass concentration), and then dried at 120° C. for 12 hours. The derived sample was heated at 700° C. for one hour in $NH_3$ flow to obtain $W_2N/AC$ containing 15 wt % of tungsten.

Example 6 is the Preparation of a Nitride Tungsten Nickel Catalyst

Active carbon was impregnated with mixed solutions of ammonium molybdate and nickel nitrate (Mo/Ni mass ration 1:1, mass concentration of ammonium molybdate 0.2 g/ml), and then dried at 120° C. for 12 hours. The derived sample was heated at 700° C. for one hour in $NH_3$ flow to obtain Ni—$W_2N/AC$ catalyst (15 wt % Ni-15 wt % W).

Example 7 is the Preparation of a Molybdenum Nitride Catalyst

Active carbon was impregnated with ammonium molybdate solution (0.3 g/ml of mass concentration), and then dried at 120° C. for 12 hours. The derived sample was heated at 700° C. for one hour in $NH_3$ flow to obtain $Mo_2N/AC$ catalyst containing 15 wt % of Mo.

Example 8 is the Preparation of a Nickel Molybdenum Nitride Catalyst

Active carbon was impregnated with mixed solutions of ammonium molybdate and nickel nitrate (Mo/Ni mass ratio of 1:1, mass concentration of ammonium molybdate 0.27 g/ml), and then dried at 120° C. for 12 hours. The derived sample was heated at 700° C. for one hour in $NH_3$ flow to obtain catalyst Ni—$Mo_2N/AC$ (15 wt % Ni-15 wt % Mo).

Example 9 is a Preparation of Molybdenum Phosphide Catalyst

A $TiO_2$ support was impregnated with mixed solutions of ammonium molybdate and diammonium phosphate (Mo/P mole ratio 1:1.2), and then dried at 120° C. for 12 hours. The derived sample was reduced at 650° C. for 2 hours in hydrogen flow to obtain a MoP/TiO$_2$ catalyst, which contains 16 wt % of Mo.

Example 10 is a Preparation of Ruthenium Molybdenum Phosphide Catalyst

A TiO$_2$ support was impregnated with mixed solutions of ammonium molybdate, diammonium phosphate, and ruthenium trichloride (Mo/P mole ratio 1:1.2, and Mo/Ru weight ratio 8:1), and then dried at 120° C. for 12 hours. The derived sample was reduced at 650° C. for 2 hours in hydrogen flow to obtain a Ru—MoP/TiO$_2$ catalyst, which contains 16 wt % of Mo and 2 wt % of Ru.

Example 11 is an Experiment of Catalytic Cellulose Conversion

Catalytic conversion of cellulose was carried out in a sealed and high pressure reactor (200 ml) typically at 5 MPa H$_2$ pressure (measured at room temperature) and 240° C. for 30 minutes. For each reaction, 1.0 g cellulose, 0.3 g catalyst and 100 ml water were put into the reactor and stirred. After the reaction, the liquid-phase products were analyzed by high-performance liquid chromatography (HPLC) and refractive index detector (R1). Cellulose conversions were determined by the change of cellulose weight before and after the reaction. The yield of polyols was calculated by the equation: yield (%)=(weight of polyol in the products)/(weight of cellulose put into the reactor)×100%. The production yield rate only calculates the target products, which are ethylene glycol and hexitols (including sorbitol and mannitol). Other liquid products comprise propylene glycol, erythritol, ethanol, unknown components, and other gas products, such as (CO$_2$, CH$_4$, C$_2$H$_6$ etc.), are not being calculated the yield thereof.

Example 12

The results of catalytic conversion of cellulose over various metal and bimetallic catalysts (Table 1). The reacting conditions are the same as the above example 11.

TABLE 1

| Catalyst | Cellulose Conversion % | Ethylene Glycol yield % | Hexahydric alcohol yield % | Others Yield % |
| --- | --- | --- | --- | --- |
| W/AC(30% W) | 100 | 5 | 2 | 93 |
| Ni—W/AC (15% Ni—25% W) | 100 | 69 | 7 | 24 |
| Pt—W/AC (0.5% Pt—75% W) | 100 | 68 | 12 | 20 |
| Pt—W/AC (0.5% Pt—15% W) | 100 | 60 | 8 | 32 |
| Ru—W/AC (0.5% Ru—15% W) | 100 | 57 | 12 | 31 |
| Mo—Ni/Al$_2$O$_3$ (15% Mo—15% Ni) | 67 | 34 | 3 | 30 |
| Pt/AC(1% Pt) | 62 | 9 | 7 | 46 |
| Ni/AC(20% Ni) | 71 | 11 | 6 | 54 |
| Ru/AC(2% Ru) | 55 | 12 | 10 | 33 |

As can be seen from the Table 1, for the catalysts having single tungsten or the metals of group 8, 9, and 10, such as Ni, Pt, or and Ru, the ethylene glycol yields are relatively lower. However, when the bimetallic catalyst comprises catalytic hydrogenating component and tungsten, the yield of ethylene glycol is significantly increased, so that the bimetallic catalyst shows the high catalytic performance thereof. For example, the reaction applying the Ni—W catalyst is able to obtain the 69% yield of ethylene glycol.

Example 13

Table 2 shows the results of the cellulose conversion over molybdenum carbide catalysts, wherein the reacting conditions are the same as the example 11 described above.

TABLE 2

| Catalyst | Cellulose Conversion % | Ethylene Glycol yield % | Hexahydric alcohol yield % | Others Yield % |
| --- | --- | --- | --- | --- |
| Mo$_2$C/AC(30% Mo) | 45 | 5 | 2 | 38 |
| Pt—Mo$_2$C/AC(2% Pt—30% Mo) | 48 | 32 | 3 | 13 |

As can be seen from the results in Table 2, when the catalyst comprises the hydrogenating active components of Pt and the molybdenum carbide, the ethylene glycol has a yield significantly higher than that of using the molybdenum carbide catalyst only.

Example 14

Table 3 shows the results of the cellulose conversion over the nitrides catalysts and phosphide catalysts, wherein the reacting conditions are the same as the example 11.

TABLE 3

| Catalyst | Cellulose Conversion % | Ethylene Glycol yield % | Hexahydric alcohol yield % | Others Yield % |
| --- | --- | --- | --- | --- |
| W$_2$N/AC(15% W) | 95 | 12 | 8 | 75 |
| W$_2$N—Ni/AC (15% W + 15% Ni) | 100 | 54 | 12 | 34 |
| Mo$_2$N/AC(15% Mo) | 65 | 6 | 3 | 56 |
| Mo$_2$N—Ni/AC (15% Mo—15% Ni) | 84 | 48 | 6 | 50 |
| MoP/TiO$_2$(16% Mo) | 69 | 4 | 2 | 63 |
| MoP—Ru/TiO$_2$ (16% Mo—2% Ru) | 76 | 31 | 9 | 26 |

Accordingly, when the molybdenum nitride, phosphide, and tungsten nitride catalysts contain group (8, 9, 10) metals, higher yields of ethylene glycol can be obtained.

Example 15

Table 4 shows the results of the cellulose conversion over the combined catalysts. The catalyst of tungsten carbide, metallic tungsten, or metallic molybdenum was physically mixed with the metallic catalysts of group (8, 9, 10) at weight ratio of 1 to 1, and tested in the reaction. The results of cellulose conversion are shown in Table 4. The reacting conditions are the same as example 11.

TABLE 4

| Catalyst | Cellulose Conversion % | Ethylene Glycol yield % | Hexahydric alcohol yield % | Others Yield % |
| --- | --- | --- | --- | --- |
| W/AC(60% W) + Pt/AC(1% Pt) | 100 | 55 | 6 | 39 |
| W/AC(60% W) | 100 | 3 | 2 | 95 |

TABLE 4-continued

| Catalyst | Cellulose Conversion % | Ethylene Glycol yield % | Hexahydric alcohol yield % | Others Yield % |
|---|---|---|---|---|
| Pt/AC(1% Pt) | 62 | 9 | 7 | 46 |
| W$_2$C/AC(30% W) + Ru/SiO$_2$ (5% Ru) | 100 | 46 | 8 | 46 |
| Ru/SiO$_2$ (5% Ru) | 75 | 12 | 10 | 53 |
| W$_2$C/AC(30% W) | 95 | 18 | 5 | 72 |
| W$_2$C/AC(30% W) + Ni/AC(20% Ni) | 100 | 43 | 2 | 56 |
| Ni/AC(20% Ni) | 65 | 13 | 8 | 44 |
| Raney Ni + W/AC(30% W) | 100 | 53 | 7 | 39 |
| Raney Ni | 25 | 4 | 1 | 20 |
| Mo/Al$_2$O$_3$(10% Mo + Pt/ZrO$_2$(3% Pt) | 72 | 32 | 6 | 34 |

As can be seen from the result shown in the Table 4, when the tungsten carbide, metallic tungsten, and molybdenum catalysts were mechanically mixed with the metallic catalysts of the group (8, 9, 10), ethylene glycol was obtained at higher yields compared with the catalysts having single active component. The combination of a skeletal catalyst such as Ni sponge and W can also lead a high yield of ethylene glycol.

Example 16

Table 5 shows the results of cellulose conversion over Ni—W/AC (15% Ni-25% W) as a function of reaction time. Except the reaction time is different, all other conditions are the same as example 11.

TABLE 5

| Reaction time | Cellulose Conversion % | Ethylene Glycol yield % | Hexahydric alcohol yield % | Others Yield % |
|---|---|---|---|---|
| 10 min | 59 | 29 | 2 | 28 |
| 30 min | 100 | 69 | 7 | 24 |
| 3 h | 100 | 51 | 11 | 38 |
| 5 h | 100 | 24 | 8 | 68 |
| 24 h | 100 | 19 | 10 | 71 |

As can be seen from the results in Table 5, the nickel-tungsten carbide catalyst has good yields of ethylene glycol within a certain reaction time. The preferred reaction time is 30 minutes to 3 hours.

Example 17

Table 6 shows the results of cellulose conversion over Ni—W/AC (15% Ni-25% W) as a function of reaction temperatures. Except the reaction temperature is different, all other conditions are the same as example 11.

TABLE 6

| Reaction temperature (° C.) | Cellulose Conversion % | Ethylene Glycol yield % | Hexahydric alcohol yield % | Others Yield % |
|---|---|---|---|---|
| 130 | 21 | 9 | 3 | 9 |
| 220 | 81 | 39 | 6 | 36 |
| 240 | 100 | 69 | 7 | 24 |
| 250 | 100 | 53 | 6 | 41 |
| 270 | 100 | 16 | 5 | 79 |

According to Table 6, the nickel-tungsten carbide catalyst added in the reaction system of the present invention for converting cellulose is able to obtain high yield of ethylene glycol. The preferred reaction temperature is in the range of 220-250° C.

Example 18

The influence of reaction pressures on the cellulose conversion. Table 7 lists the results of cellulose conversion over Ni—W/AC (15% Ni-25% W) catalyst under different reaction pressures. Except the reaction pressures, all other reaction conditions are the same as example 11.

TABLE 7

| Hydrogen pressure (MPa) | Cellulose Conversion % | Ethylene Glycol yield % | Hexahydric alcohol yield % | Others Yield % |
|---|---|---|---|---|
| 2 | 33 | 8 | 4 | 21 |
| 3 | 89 | 36 | 5 | 48 |
| 5 | 100 | 69 | 7 | 24 |
| 6 | 100 | 56 | 8 | 36 |
| 7 | 100 | 53 | 6 | 41 |
| 12 | 100 | 33 | 4 | 63 |

According to the Table 7, the nickel-tungsten carbide catalyst in the reaction system of the present invention for converting cellulose is able to obtain high yield of the ethylene glycol under various hydrogen pressures. The preferred reaction pressure is between 3 MPa to 7 MPa.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of preparing ethylene glycol from cellulose, which comprises the steps of:
   providing said cellulose as a raw reacting material;
   catalytically hydrogenating said cellulose with water in a sealed and high pressure reactor; wherein a catalyst, which is added for catalyzing said cellulose, comprises two sorts of active components, ascribed to a first active group and a second active group, wherein a first active component of said first active group is one or more metals selected from the group consisting of iron, cobalt, nickel, ruthenium, rhodium, palladium, iridium, and platinum of the group 8, 9, or 10 transition metals, wherein a second active component of the second active group is one or more materials selected from the group consisting of metallic state molybdenum, metallic state tungsten, molybdenum carbides, molybdenum nitrides, molybdenum phosphides, tungsten carbides, tungsten nitrides, and tungsten phosphides; and
   stirring said cellulose within said sealed and high pressure reactor, wherein a hydrogen gas within said reactor at room temperature has an initial pressure in the range of 1 to 12 MPa, wherein a reacting temperature is in the range of 120 to 300° C., wherein a reacting time is equal or longer than 5 minutes;

wherein a weight ratio of said second active component of said second active group to said first active component of said first active group is in the range of 0.02 to 1600.

2. The method, as recited in claim 1, wherein said catalyst is a supported catalyst as a support to load said active components, wherein said support is one or more compositions selected from the group consisting of active carbon, alumina, silica, zirconia, zinc oxide, and titanium dioxide, wherein metallic content of said first active component of said first active group is 0.05 to 50 wt % at said support, and metallic content of said second active component of said second active group is 1 to 80 wt % at said support.

3. The method, as recited in claim 2, wherein said metallic content of said first active component of said first active group is 1 to 30 wt % at said support, and metallic content of said second active component of said second active group is 10 to 60 wt % at said support.

4. The method, as recited in claim 1, wherein said catalyst is a non-supported type that the framework of a metallic skeletal catalyst is made of said active groups.

5. The method, as recited in claim 1, wherein said first active component is mechanically mixed with said second active component, wherein said first active component is one or more metals selected from the group consisting of iron, cobalt, nickel, ruthenium, rhodium, palladium, iridium, and platinum of the group 8, 9, or 10 transition metals, wherein said second active component is tungsten carbide, wherein a weight ratio of said second active component and said first active component is 0.02 to 1600 times.

6. The method, as recited in claim 1, wherein a mass ratio of said cellulose of said raw material to water is 1:200 to 1:4, wherein a mass ratio of said cellulose to said catalyst is 1:1 to 30:1.

7. The method, as recited in claim 1, wherein preferably said reacting temperature is in the range of 220 to 250° C., wherein preferably said hydrogen gas within said reactor at room temperature has an initial pressure 3 to 7 Mpa, wherein preferably said reacting time is 30 minutes to 3 hours.

8. The method, as recited in claim 1, wherein preferably the weight ratio of said second active component to said first active component is in the range of 0.3 to 60 times.

* * * * *